(12) United States Patent
Borgers et al.

(10) Patent No.: US 8,147,852 B2
(45) Date of Patent: Apr. 3, 2012

(54) MODIFIED AZOLE COMPOUNDS AS ANTIFUNGAL AND ANTIBACTERIAL AGENTS

(75) Inventors: Marcel Borgers, Knokke (BE); Maarten van Geffen, Beerse (BE); Jannie Ausma, Goirle (NL)

(73) Assignee: Barrier Therapeutics, Inc., Princeton, NJ (US)

( * ) Notice: Subject to any disclaimer, the term of this patent is extended or adjusted under 35 U.S.C. 154(b) by 514 days.

(21) Appl. No.: 12/108,262

(22) Filed: Apr. 23, 2008

(65) Prior Publication Data
US 2008/0213398 A1 Sep. 4, 2008

Related U.S. Application Data

(63) Continuation of application No. 11/591,609, filed on Nov. 2, 2006.

(60) Provisional application No. 60/835,085, filed on Aug. 3, 2006.

(51) Int. Cl.
*A61K 9/00* (2006.01)
*A61K 31/415* (2006.01)
*A61K 31/065* (2006.01)

(52) U.S. Cl. .......... 424/400; 514/396; 514/726
(58) Field of Classification Search .......... 424/400; 514/396, 728
See application file for complete search history.

(56) References Cited

U.S. PATENT DOCUMENTS

| 4,911,432 A | 3/1990 | Walden | 424/642 |
| 5,061,700 A * | 10/1991 | Dow et al. | 514/169 |
| 6,001,864 A | 12/1999 | Akashi et al. | 514/399 |

FOREIGN PATENT DOCUMENTS
WO   WO 98/43673   10/1998

OTHER PUBLICATIONS

Zhang et al. "Structure and generation mechanism of a novel degradation product formed by oxidatively induced coupling of miconazole nitrate with butylated hydroxytoluene in a topical ointment studied by HPLC-ESI-MS and organic synthesis" J. Pharmaceutical Sciences 93(2):300-309 (2004).

* cited by examiner

*Primary Examiner* — Shengjun Wang
(74) *Attorney, Agent, or Firm* — The Nath Law Group; Joshua B. Goldberg

(57) ABSTRACT

The present invention relates to the compounds of formula (I), their preparation and use as antifungal and/or antibacterial agents.

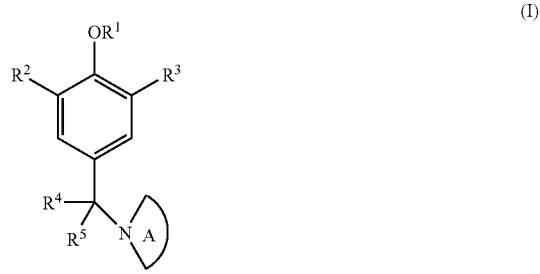

where the values for $R^1$, $R^2$, $R^3$, $R^4$, $R^5$ and A are as defined herein.

18 Claims, 3 Drawing Sheets

MODIFIED AZOLE COMPOUNDS AS ANTIFUNGAL AND ANTIBACTERIAL AGENTS

RELATED APPLICATIONS

This is a continuation application of U.S. application Ser. No. 11/591,609 (filed Nov. 2, 2006), which claims the benefit of U.S. Provisional Application No. 60/835,085 (filed Aug. 3, 2006), both of which are herein incorporated by reference in their entireties.

FIELD OF THE INVENTION

The present invention relates to various modified azole compounds and their preparation and use as antifungal and/or antibacterial agents.

BACKGROUND OF THE INVENTION

The increasing global incidence of systemic fungal infections may largely be attributed to advances in medical technology and organ transplantation, an increase in the prevalence of cytotoxic chemotherapeutic interventions, the widespread use of broad spectrum antimicrobials and an increasing number of immunocompromised patients.

The most common causes of these infections are due to *Candida* spp., of which *C. albicans* accounts for approximately 50% and filamentous fungi such as *Aspergillus* spp. (Kremery and Barnes, 2002). Mortality associated with invasive *Candida* ranges from around 40% (Edmond et al., 1999), while mortality associated with invasive *Aspergillus* approaches 100% in solid organ transplant recipients (Minari et al., 2002).

Given the lack of readily available fungal vaccines, the only clinical resource available to combat fungal infections is antifungal therapeutics (antimycotics). The antimycotics currently in clinical use are limited either by their general ineffectiveness and inadequate pharmacological profile, including undesired drug-drug interactions and narrow activity spectrum, their fungistatic nature, or by their high overall cytotoxicity (White et al., 1998). Accordingly, there is a critical need for new antifungal compounds that could overcome these disadvantages.

Zhang et al. recently reported the formation of a 1:1 adduct of the antifungal azole compound miconazole nitrate with 2,6-di-tert-butyl-4-methylphenol (BHT) (Zhang et al., 2004). The present invention relates in part to the unexpectedly enhanced antifungal activity exhibited by this adduct as well as by adducts of BHT with other azole compounds and adducts of compounds of formula (I) other than BHT with miconazole nitrate and other azole compounds.

SUMMARY OF THE INVENTION

An aspect of the invention is a method of treating fungal and/or bacterial disorders comprising systemically or topically administering to a recipient in need of such treatment an effective amount of a compound of the formula (I)

wherein $R^1$=—H, alkyl, —C(O)$R^6$, —C(O)O$R^6$ or —S(O)$_n R^6$; $R^2$, $R^3$, $R^4$ and $R^5$ independently=—H or alkyl; A=an azole; $R^6$=alkyl, aryl or heteroaryl; and n=1 or 2, or a pharmaceutically acceptable salt thereof.

Another aspect of the invention is a method of treating fungal and/or bacterial disorders comprising systemically or topically administering to a recipient in need of such treatment an effective amount of a compound or a pharmaceutically acceptable salt of the compound formed by the combination of di-tert-butyl-4-methylphenol (BHT) with an azole.

Another aspect of the invention is a pharmaceutical composition comprising a compound of the formula (I)

wherein $R^1$=—H, alkyl, —C(O)$R^6$, —C(O)O$R^6$ or —S(O)$_n R^6$; $R^2$, $R^3$, $R^4$ and $R^5$ independently=—H or alkyl; A=an azole; $R^6$=alkyl aryl or heteroaryl; and n=1 or 2, or a pharmaceutically acceptable salt thereof.

Yet another aspect of the invention is a pharmaceutical composition comprising an adduct of BHT or a compound of formula (I) other an BHT with an azole-containing compound selected from the group consisting of miconazole, clotrimazole, econazole, fluconazole, itraconazole, ketoconazole, pramiconazole, sertaconazole, butoconazole, ravuconazole, voriconazole, posaconazole, luliconazole and pharmaceutically acceptable salts thereof.

Another aspect of the invention is compound of formula (I)

wherein $R^1$=—H, alkyl, —C(O)$R^6$, —C(O)O$R^6$ or —S(O)$_n R^6$; $R^2$, $R^3$, $R^4$ and $R^5$ independently=—H or alkyl; A=an azole; $R^6$=alkyl, aryl or heteroaryl; and n=1 or 2, or a pharmaceutically acceptable salt thereof, with the proviso that $R^1$ is not —H when $R^2$ and $R^3$ are tert-butyl, $R^4$ and $R^5$ are —H, and A is miconazole.

DETAILED DESCRIPTION OF THE INVENTION

Definitions

Unless defined otherwise, all technical and scientific terms used herein generally have the same meaning as commonly understood by one of ordinary skill in the art to which this invention belongs.

As defined herein, "effective amount" or "an amount effective to" or a "therapeutically effective amount" or any grammatically equivalent term refers to the amount that, when administered to an animal for treating a disease or condition, is sufficient to effect treatment for that disease or condition.

As defined herein, "topical administration" is used in the conventional sense to mean delivery of a topical drug or pharmacologically active agent directly to the skin or mucosa of an individual.

As defined herein, an "antifungal agent" is an agent that inhibits the growth of fungi (i.e., a fungistat) and/or kills them outright (i.e., a fungicide).

As defined herein, a "skin fungal disorder" is intended to encompass all fungal disorders that affect skin, hair, nail, oral and genital mucosa as well as internal organs and blood. A "bacteria disorder" is intended to encompass any bacterial disorder, including, but not limited to those that affect skin, hair, nails, oral and genital mucosa as well as internal organs and blood. In an exemplary embodiment, the bacterial disorder is a Gram+bacterial disorder.

As defined herein, an "adduct" is a single chemical compound formed by the combination of at least two other chemical compounds. The adducts of the present invention typically exist in a salt form.

As defined herein, an "azole" is a member of a class of optionally substituted five-membered ring heterocyclic compounds containing two double bonds, a nitrogen atom and at least one other atom selected from nitrogen, sulfur and oxygen. "Azole" is also used more broadly to refer to a compound that contains within its structure at least one azole moiety. The term "azole" as well as the recitation of a particular azole, may include both the neutral compound and any corresponding salt. For example, the term "miconazole" as an exemplary azole, may be used to refer both the neutral compound and to a salt thereof, such as miconazole nitrate.

As defined herein, the term "rambazole" refers to the compound benzothiazol-2-yl-[4-(2-ethyl-1-[1,2,4]triazol-1-yl-butyl)-phenyl]-amine, including pharmaceutically acceptable salts thereof. The chemical structure of rambazole is indicated below:

As defined herein, the term "alkyl," by itself or as part of another substituent refers to, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, methylene, ethylene and homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

As defined herein, the term "aryl" refers to, unless otherwise stated, a polyunsaturated, optionally substituted aromatic, substituent that can be a single ring or multiple rings (preferably from 1 to 3 rings), which are fused together or linked covalently. The term "heteroaryl" refers to optionally substituted aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, alkylaryl) includes both aryl and heteroaryl rings as defined above. Thus, as defined herein, the term "alkylaryl" refers to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "aryl" and "heteroaryl") is meant to include both substituted and unsubstituted forms of the indicated radical. Preferred substituents for each type of radical are provided below.

Substituents for the alkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(R'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR'), —X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As defined herein, the term "heteroatom" refers to include oxygen (O), nitrogen (N), sulfur (S) and silicon (Si).

In an exemplary embodiment, the adduct is a 1:1 combination of the compound of formula (I) with an azole. In a particular embodiment, the adduct is a 1:1 combination of BHT with an azole.

In a particular embodiment of the invention, R$^1$ is —H.

In another particular embodiment, R$^1$ is —C(O)R$^6$.

In another particular embodiment, R$^2$ and R$^3$=alkyl and R$^4$ and R$^5$=—H.

In another particular embodiment, R$^1$, R$^4$ and R$^5$=—H, and R$^2$ and R$^3$=alkyl.

In another particular embodiment, R$^1$=—C(O)R$^6$, R$^4$ and R$^5$=—H, and R$^2$ and R$^3$=alkyl.

In an aspect of the invention, the azole includes, but is not limited to, ketoconazole, itraconazole, pramiconazole, miconazole, metronidazole, liarozole, rambazole, benzimidazole, benzothiazole, bifonazole, butaconazole nitrate, climbazole, clotrimazole, croconazole, eberconazole, albaconazole, econazole, elubiol, fenticonazole, fluconazole, flutimazole, isoconazole, lanoconazole, neticonazole, omoconazole, oxiconazole nitrate, sertaconazole, sulconazole, tioconazole, thiazole, terconazole, posaconazole, voriconazole, ravuconazole, luliconazole and pharmaceutically acceptable salts thereof. In an exemplary embodiment, the azole is selected from the group consisting of itraconazole, ketoconazole and pramiconazole. While the methods of the invention are intended to include the adduct of BHT with miconazole, this adduct is specifically excluded from the novel compounds of the invention.

Suitable pharmaceutical acceptable salts are those of organic or inorganic acids, including, but not limited to, hydrochloric acid, hydrobromic acid, hydroiodic acid, sulfuric acid, nitric acid, phosphoric acid, acetic acid, succinic acid, oxalic acid, malic acid and the like.

It is intended that the present invention include within its scope any stereochemically pure isomeric forms of the azoles as well as their racemates. Stereochemically pure isomeric forms may be obtained by the application of known principles. For example, diastereoisomers may be separated by physical separation methods such as fractional crystallization and chromatographic techniques, and enantiomers may be separated from each other by the selective crystallization of the diastereomeric salts with optically active acids or by chiral chromatography. Pure isomers may also be prepared synthetically from appropriate stereochemically pure starting materials, or by using stereospecific reactions.

The compounds of formula (I) are intended to include prodrugs that exhibit superior solubility and/or bioavailability properties compared to the parent compounds to which the prodrugs are converted in vivo (i.e., metabolized). In an exemplary embodiment, both the prodrug and the metabolite exhibit antifungal properties. In another exemplary embodiment, the metabolite but not the prodrug exhibits antifungal properties. The prodrugs of formula (I) may be prepared by any methods known in the art. In an exemplary embodiment, the oxygen atom attached to the phenyl ring of compound serves as a means of creating prodrugs. In a particular embodiment, the oxygen atom forms an ester. In another particular embodiment, the oxygen atom forms a carbonate. In another particular embodiment, the oxygen atom forms an ether.

In an exemplary embodiment, the compounds of formula I are prepared by combining a known azole with a phenyl derivative of formula (II) containing a benzylic hydrogen as shown below. A mechanism for this coupling reaction is proposed in Zhang et al., 2004. In a particular embodiment, the compound of formula (II) is BHT (i.e., where $R^1$=H, $R^2$ and $R^3$=t-butyl, and $R^4$ and $R^5$=H).

Typical skin fungal disorders that are treatable by the described adducts of BHT with azole-containing compounds include those, but are not limited to, for example, associated with *Candida* spp., *Pityrosporum* spp., *Malassezia* spp. and *Trichophyton* spp. Exemplary embodiments of *Candida* spp. include, but are not limited to, *Candida albicans, Candida tropicalis, Candida glabrata, Candida parapsiliosis, Candida guilliermondi, Candida lusitaniae* and *Candida krusei*. Exemplary embodiments of *Trichophyton* include, but are not limited to, *Trichophyton mentagrophytes* and *Trichophyton rubrum*. Exemplary embodiments of *Pityrosporum* include, but are not limited to, *Pityrosporum orbiculare, Pityrosporum ovale, Pityrosporum canis* and *Pityrosporum pachydermatis*. Exemplary embodiments of *Malassezia* include, but are not limited to, *Malassezia sympodialis, Malassezia globosa, Malassezia restricta, Malassezia slooffiae, Malassezia furfur, Malassezia obtusa* and *Malassezia pachydermatis*.

Candidiasis is a common mycotic infection, especially in immunocompromised hosts, that contributes to a variety of diseases, such as, but not limited to, vaginitis, vulvovaginitis, vulvar rash, oral thrush, conjunctivitis, oropharyngeal candidiasis, endophthalmitis, diaper rash, nail infections, infections of skin folds, systemic candidiasis, oral candidiasis, gastrointestinal candidiasis and red macerated intertriginous areas.

Additional diseases caused by fungi other *Candida* that may be treated by the compounds of the invention include, for example, Aspergillosis, Blastomycosis, Coccidioidomycosis, Cryptococcosis, Histoplasmosis, Paracoccidioidomycosis, Sporotrichosis and Zygomycosis.

Infections associated with gram positive bacteria such as, for example, Staphylococci and Streptococci, as well as *Propionibacterium acnes* are also effectively treated by the compounds of the invention.

Formulations for the compounds of formula (I) include, for example, solutions, ointments, salves, creams, gels, lotions, foams, dressings, shampoos, tinctures, pastes, tablets, capsules, intravenous or other parenteral formulations, mucoadhesive patches, powders and the like. Anhydrous formulations may be preferred for some applications. Application of the compositions of the invention may also be by aerosol, e.g., with a propellant such as nitrogen, carbon dioxide, a freon, or without a propellant such as a pump spray, drops, lotions, or a semisolid such as a thickened composition which can be applied by a swab. In addition, the compounds of the invention may be applied as a transdermal patch. Other suitable routes of administration include intravenous and oral applications, in, for example, solution form, of the compounds.

Other suitable formulations include toilet waters, packs, skin milks or milky lotions. Such formulations often include therapeutically inactive components such as those known in the art, such as, for example, oils, fats, waxes, surfactants, humectants, thickening agents, antioxidants, viscosity stabilizers, chelating agents, buffers, preservatives, perfumes, dyestuffs and the like. If desired, additional ingredients may be incorporated in the compositions of the invention such as antiinflamatory agents, antibacterials, antifungals, disinfectants, vitamins, sunscreens, antibiotics or anti-acne agents.

Solid carriers include starch, lactose, dicalcium phosphate, microcrystalline cellulose, sucrose, kaolin. Liquid carriers include sterile water, propylene glycol, glycerin, ethylene glycol, polyethylene glycols, lower alcohols (e.g., ethanol, propanol, isopropanol and butanol) and edible oils such as corn, peanut and sesame oils. In exemplary embodiments, the carriers may be present in an amount of from about 5 to about 80 weight percent, such as, for example, about 10 to about 70 weight percent, such as, for example, about 15 to about 60 weight percent, such as about 15 to about 45 weight percent, such as about 15 to about 30 weight percent, such as about 15 to about 20 percent, such as about 20 to about 55 weight percent; such as about 25 to about 45 weight percent, such as, for example, about 30 to about 40 weight percent.

In an exemplary embodiment, the compounds of formula (I) are present in an ointment formulation that also includes zinc oxide and a petrolatum. In a particular embodiment, an adduct of BHT with an azole is formulated as an ointment containing zinc oxide, white petrolatum, trihydroxystearin and optionally a fragrance.

The pharmaceutical compositions of the invention may also optionally include other carriers, stabilizers, preservatives or adjuvants. For typical examples of these classes of compounds, see *Remington: The Science and Practice of Pharmacy*, Lippincott, Williams & Wilkins (2005), which is incorporated by reference in its entirety.

An effective amount of the compounds of formula (I) may vary depending on the particular compound used; the mode of administration; the identity and severity of the disease state; the age, sex, weight and general physical condition of the particular recipient; and other medications that the recipient may be concurrently taking. Furthermore, it is evident that the effective frequency of administration of the combination therapy may be lowered or increased depending on the response of the treated patient and/or depending on the evaluation of the physician prescribing the therapeutic agent being used. In general, satisfactory results are obtained when the amount of the active compound used ranges from about 0.01 weight percent to about 10 weight percent, such as from about 0.01 to about 5 weight percent, and such as from about 0.05 to about 3 weight percent or from about 0.1 to about 3 weight percent. It may be appropriate to administer the compounds of formula (I) either alone or in a combination therapy, once daily or as two, three, four or more sub-doses at appropriate intervals throughout the day. Sub-doses may be formulated as unit dosage forms, for example, containing 0.001 mg to 500 mg of active ingredient per unit dosage form.

In exemplary embodiments, the effective relative amount (w/w) of BHT to the azole (with which the BHT forms an adduct) necessary for treating a fungal disease state is about 0.1% or about 0.5% or about 1% or about 5% or about 10% or about 15% or about 20% or about 25% or about 30% or about 35% or about 40% or about 45% or about 50% or about 55% or about 60% or about 65% or about 70% or about 75% or about 80% or about 85% or about 90% or about 95% or about 100%. In particular embodiments, the azole is miconazole, ketoconazole, rambazole, itraconazole or pramiconazole.

Additional therapeutic agents that may be used in combination with the compounds of formula (I) include, but are not limited to, antimicrobial agents (e.g, amphotericin B, flucytosine, haloprogin and nystatin), anti-allergic agents (e.g., astemizole, betamethasone, carbinoxamine maleate, chlorpheniramine maleate, clemastine fumarate, dexbrompheniramine maleate, dexchlorpheniramine maleate, diphenhydramine hydrochloride, diphenylpyraline hydrochloride and trimeprazine tartrate), anti-inflammatory agents (e.g., ibuprofen, fenoprofen, ketoprofen, naproxen, diclofenac, etodolac, meclofenamate sodium phenylbutazone, indomethacin, piroxicam, sulindac and tolmetin), anti-proliferating agents (e.g., mycophenolate mofetil and evodiamine), anti-acne agents (e.g., tretinoin, isotretinoin, salicylic acid, benzoyl peroxide and azelaic acid), anti-pruritic agents (e.g. azelastine, cetirizine permethrin and lindane), anti-aging agents and combinations thereof.

Without further description, it is believed that one of ordinary skill in the art can, using the preceding description and the following illustrative examples, make and utilize the compounds of formula (I) and practice the claimed methods. The following working examples describe exemplary embodiments of the present invention, and are not to be construed as limiting in any way the remainder of the disclosure.

EXPERIMENTAL

Example 1

Background: The objective of this study was to compare the antifungal effects of an ointment formulation containing miconazole nitrate, white petrolatum and zinc oxide, but no BHT) ("Sample A") with an ointment formulation containing miconazole nitrate, white petrolatum, zinc oxide and BHT, where the amount of BHT (w/w) relative to the amount of miconazole nitrate ranges from about 1% to about 2%) ("Sample B"). The tested concentrations of Sample A and Sample B were 100%, 50%, 25%, 12.5% and 6.25%.

Experimental: A clinical isolate of *Candida albicans* was subcultured and incubated at 30° C. for 24 hours. An inoculum of 1×10 mL was prepared spectrophotometrically by adding the yeast to water and adjusting to 85% T on the spectrophotometer. This inoculum was diluted 1:100 in sterile distilled water for a working concentration of $1 \times 10^3$ CFU/mL. Assessment of antifungal activity took place by two different methods. The first method involved weighing 10 mg of the Sample A and Sample B ointments, suspending them separately in 1 mL of PEG 400, and evenly spreading the resulting ointment solutions separately across the surface of a Sabouraud Dextrose Agar plate. A 10 µL volume of the yeast suspension was spread across the surface of the agar to achieve confluent yeast growth. The tested concentrations of Sample A and Sample B were 100%, 50%, 25%, 12.5% and 6.25%. To achieve these dilutions, approximately 10 mg of the respective ointment solutions were added to PEG-400 volumes of 2 mL, 4 mL, 8 mL, and 16 mL respectively. Plates were incubated at 30° C. and CFU counts were performed at 48 hours post inoculation.

Figure 1:
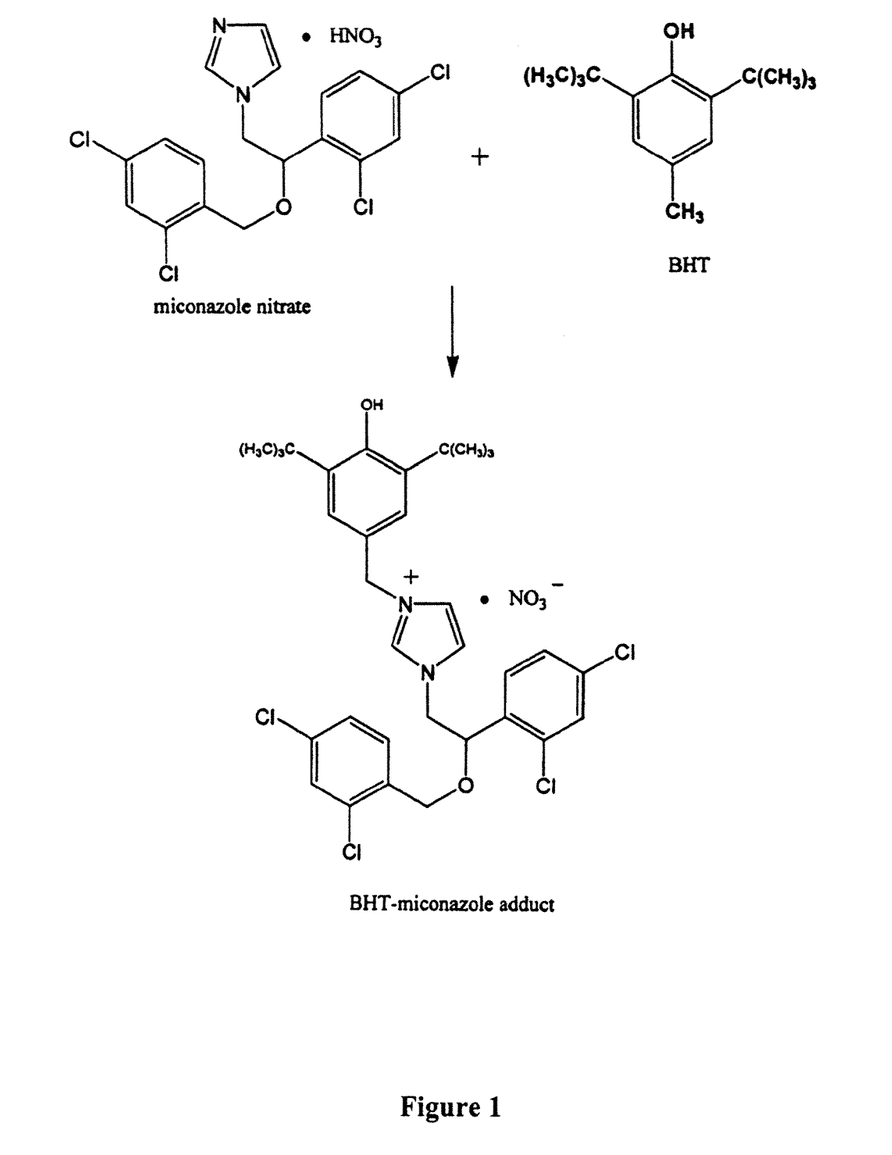
FIG. 1 depicts an exemplary embodiment of a compound of formula (I), which is the adduct miconazole nitrate and BHT.
Figure 2:
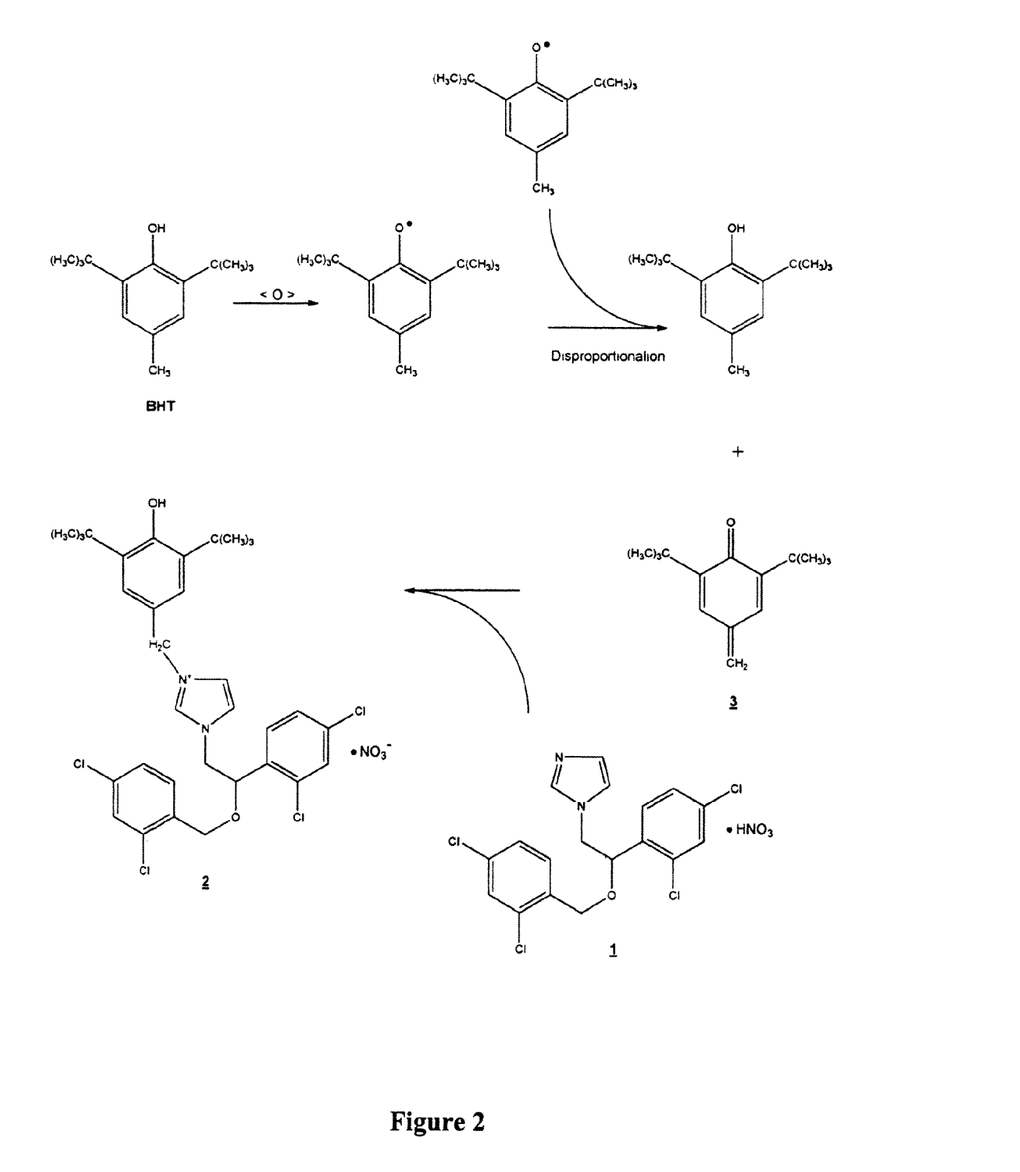
FIG. 2 depicts a proposed reaction mechanism between miconazole nitrate (i.e., an exemplary azole) and BHT (i.e., an exemplary compound of formula II) to form the miconazole nitrate—BHT adduct as a salt (i.e., an exemplary compound of formula I).
Figure 3:
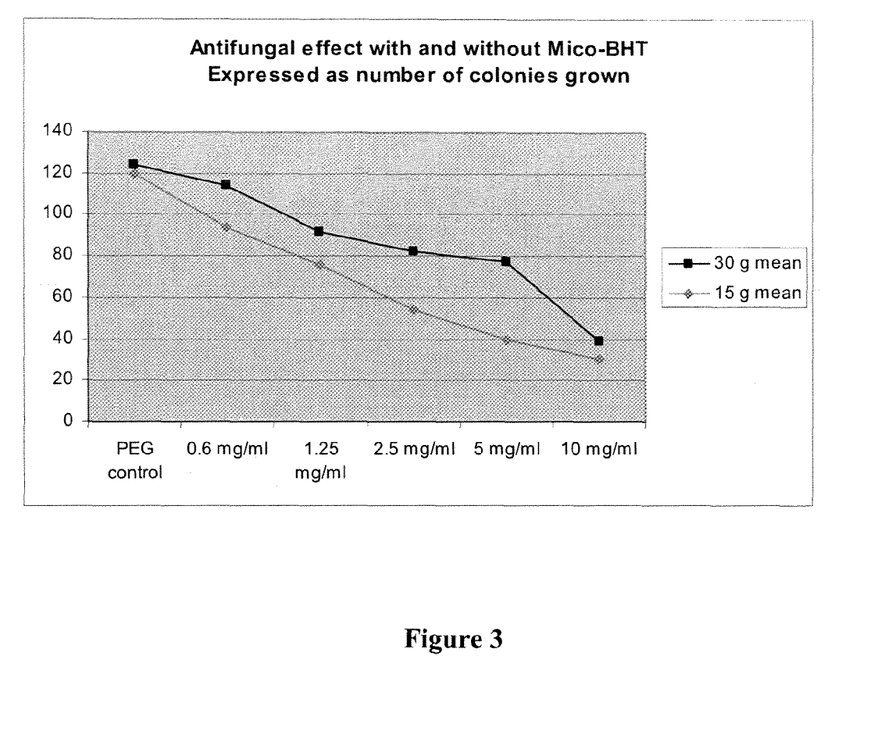
FIG. 3 depicts a comparison of the antifungal effect of miconazole nitrate (■) with the compound representing the adduct of miconazole nitrate with BHT (♦).

Results: As shown in Table 1 below and in FIG. 3, a direct correlation was observed to exist between the concentration of the active compound in the ointments and the number of CFU/mL. As the concentration of the active compound increased, the CFU/mL decreased. In an unexpected observation, the Sample B ointment (identified in Table 1 and FIG. 3 as "30 g" was significantly more potent at all tested concentrations as an antifungal against *Candida albicans* than the Sample A ointment identified in Table 1 and FIG. 3 as "15 g". Since the only difference between the Sample A and Sample B ointments was the presence of BHT, it was proposed that that the BHT-miconazole adduct (the presence of which in Sample B was confirmed by analysis (see Zhang et al., 2004), was a significantly more potent antifungal agent than miconazole alone. Table 1 shows four repetitions of the test as described above to ensure reproducibility of the obtained results.

TABLE 1

Comparison of antifungal activity of Sample A and Sample B ointment formulations

| | 30 g | 30 g | 30 g | 30 g | 30 g (mean) | 15 g | 15 g | 15 g | 15 g | 15 g (mean) |
|---|---|---|---|---|---|---|---|---|---|---|
| PEG only (control) | 112 | 121 | 134 | 111 | 120 | 109 | 133 | 130 | 120 | 123 |
| 0.6 mg/mL | 73 | 99 | 103 | 98 | 93 | 88 | 127 | 120 | 112 | 112 |
| 1.25 mg/mL | 42 | 89 | 95 | 76 | 76 | 47 | 118 | 108 | 92 | 91 |
| 2.5 mg/mL | 38 | 67 | 61 | 51 | 54 | 40 | 108 | 100 | 79 | 82 |
| 5 mg/mL | 24 | 49 | 45 | 47 | 41 | 32 | 98 | 91 | 81 | 76 |
| 10 mg/mL | 20 | 32 | 35 | 30 | 29 | 24 | 51 | 41 | 38 | 39 |

In Table 2 below, the antifungal potency of an exemplary compound of formula (I) (i.e., the species represented by the adduct of BHT with miconazole nitrate) is compared to miconazole alone against representative fungi.

TABLE 2

MIC₁₀₀ values for miconazole-BHT adduct and miconazole as measured against various fungi

| MIC₁₀₀(μM) | C. albicans | C. albicans | C. albicans | C. glabrata | C. glabrata | C. glabrata | C. tropicalis |
|---|---|---|---|---|---|---|---|
| 48 h | 19457(w.t) | 19507(r) | 20126(r) | 19371(w.t.) | 05/1032(r) | 05/1414(r) | 19596(w.t) |
| miconazole | 4.17 | 4.17 | 17 | 4.17 | 8.3 | 17 | 8.3 |
| miconazole-BHT | 2.98 | 2.98 | 2.98 | 2.98 | 5.96 | 2.98 | 2.98 |

(r) = resistant; (w.t.) = wild type

Although any methods and materials, similar or equivalent to those described herein, can be used in the practice or testing of the present invention, the preferred methods and materials are described herein. All publications, patents and patent applications cited herein are incorporated herein by reference for the purpose of disclosing and describing specific aspects of the invention for which the publication is cited.

REFERENCES

Kremery, V.; Barnes, A. J., *Hosp. Infect.*, 2002, 50, 243.
Edmond, M. B.; Wallace, S. E.; McClish, D. K.; Pfaller, M. A.; Jones, R. N.; Wenzel, R. P., *Clin. Infect. Dis.*, 1999, 29, 239.
Minari, A.; Husni, R.; Avery, R. K.; Longworth, D. L.; DeCamp, M.; Bertin, M.; Schilz, R.; Smedira, N.; Haug, M. T.; Mehta, A.; Gordon, S. M., *Transpl. Infect. Dis.*, 2002, 4, 195.
White, T. C.; Marr, K. A.; Bowden, R. A., "Clinical, Cellular, and Molecular Factors That Contribute to Antifungal Drug Resistance," *Clin. Microbiol. Rev.* 1998, 11, 382-402.
Zhang, F.; Nunes, M.; *J. Pharmaceutical Sciences* 2004, 93(2), 300-309.

We claim:

1. A method of treating a human suffering from candidiasis, comprising topically administering to the human an effective amount of a pharmaceutical composition, wherein the pharmaceutical composition is in the form of an ointment and comprises a compound of the formula 2. The method according to claim 1, wherein the pharmaceutical composition further comprises miconazole nitrate.
3. The method according to claim 1, wherein the pharmaceutical composition further comprises 2,6-di-tert-butyl-4-methylphenol.
4. The method according to claim 1, wherein the pharmaceutical composition further comprises zinc oxide.
5. The method according to claim 1, wherein the pharmaceutical composition further comprises a petrolatum.
6. The method according to claim 5, wherein the petrolatum is white petrolatum.
7. The method according to claim 1, wherein the pharmaceutical composition further comprises trihydroxystearin.
8. The method according to claim 1, wherein the candidiasis is caused by a *Candida* spp, selected from the group consisting of *Candida albicans, Candida tropicalis, Candida glabrata, Candida parapsiliosis, Candida guilliermondi, Candida lusitaniae* and *Candida krusei.*
9. The method according to claim 8, wherein the *Candida* spp, is *Candida albicans.*
10. The method according to claim 1, wherein the human is also suffering from diaper rash.
11. A method of treating a human suffering from candidiasis, comprising topically administering to the human an effective amount of a pharmaceutical composition, wherein the pharmaceutical composition is in the form of an ointment and comprises a compound of the formula miconazole nitrate;
zinc oxide;
white petrolatum; and
trihydroxystearin.

12. The method according to claim 11, wherein the candidiasis is caused by a *Candida* spp, selected from the group consisting of *Candida albicans, Candida tropicalis, Candida glabrata, Candida parapsiliosis, Candida guilliermondi, Candida lusitaniae* and *Candida krusei.*
13. The method according to claim 12, wherein the *Candida* spp, is *Candida albicans.*

14. The method according to claim 11, wherein the human is also suffering from diaper rash.

15. A method of treating a human suffering from candidiasis, comprising topically administering to the human an effective amount of a pharmaceutical composition, wherein the pharmaceutical composition is in the form of an ointment and consists of a compound of the formula miconazole nitrate;

zinc oxide;

white petrolatum;

trihydroxystearin; and optionally a fragrance.

16. The method according to claim 15, wherein the candidiasis is caused by a *Candida* spp, selected from the group consisting of *Candida albicans, Candida tropicalis, Candida glabrata, Candida parapsiliosis, Candida Candida Iusitaniae* and *Candida krusei*.

17. The method according to claim 16, wherein the *Candida* spp, is *Candida albicans*.

18. The method according to claim 15, wherein the human is also suffering from diaper rash.

* * * * *

UNITED STATES PATENT AND TRADEMARK OFFICE
CERTIFICATE OF CORRECTION

PATENT NO. : 8,147,852 B2
APPLICATION NO. : 12/108262
DATED : April 3, 2012
INVENTOR(S) : Borgers et al.

It is certified that error appears in the above-identified patent and that said Letters Patent is hereby corrected as shown below:

Claim 16, Column 14, Lines 14

Please insert: --guilliermondi,-- after "Candida parasiliosis, Candida" and before "Candida lusitaniae"

Signed and Sealed this
Seventeenth Day of July, 2012

David J. Kappos
*Director of the United States Patent and Trademark Office*